United States Patent [19]

Haughton et al.

[11] Patent Number: 5,376,075
[45] Date of Patent: Dec. 27, 1994

[54] CATHETER SHARP RETRACTION SYSTEM

[76] Inventors: Victor M. Haughton, 1071 Waterville Rd., Oconomowoc, Wis. 53066; Anton H. Clemens, 5854 Schumann Dr., Madison, Wis. 53711

[21] Appl. No.: 114,473

[22] Filed: Aug. 31, 1993

[51] Int. Cl.$^5$ .............................................. A61M 5/00
[52] U.S. Cl. ................................. 604/158; 604/171; 604/164
[58] Field of Search ................ 604/164–171, 604/158, 110, 198, 263, 272–274

[56] References Cited

U.S. PATENT DOCUMENTS

| | | |
|---|---|---|
| 2,722,215 | 11/1955 | Dahlgren . |
| 2,841,143 | 7/1958 | Bertram . |
| 3,825,003 | 7/1974 | Kruck . |
| 4,009,716 | 3/1977 | Cohen . |
| 4,573,976 | 3/1986 | Sampson et al. . |
| 4,664,259 | 5/1987 | Landis . |
| 4,676,783 | 6/1987 | Jagger et al. . |
| 4,747,831 | 5/1988 | Kulli . |
| 4,767,413 | 8/1988 | Haber et al. . |
| 4,781,692 | 11/1988 | Jagger et al. ............... 604/171 X |
| 4,826,484 | 5/1989 | Haber et al. . |
| 4,838,869 | 6/1989 | Allard . |
| 4,874,382 | 10/1989 | Lindemann et al. . |
| 4,955,870 | 9/1990 | Ridderheim et al. . |
| 4,994,034 | 2/1991 | Botich et al. . |
| 5,000,736 | 3/1991 | Kaufhold, Jr. et al. . |
| 5,108,376 | 4/1992 | Bonaldo ...................... 604/171 |
| 5,207,647 | 5/1993 | Phelps ......................... 604/158 |
| 5,215,528 | 6/1993 | Purdy et al. ................. 604/164 |

*Primary Examiner*—John D. Yasko
*Attorney, Agent, or Firm*—Andrus, Sceales, Starke & Sawall

[57] ABSTRACT

A trocar and catheter assembly for automatically disarming the trocar after placement of the catheter into a patient's blood vessel includes a spring urging retraction of the trocar and a releasable retainer mechanism for maintaining the trocar in an extended position during insertion of the catheter into the blood vessel. In one embodiment, the catheter is removably mounted to a handle which defines an internal passage. Disengaging the handle from the catheter after placement of the catheter into the blood vessel actuates the releasable retainer mechanism for allowing the trocar to be drawn into the handle passage under the influence of a spring, to enclose the sharpened end of the trocar after use. In another embodiment, the insertion device is in the form of a pair of wings which are movable between a closed position and an open position. The wings are in their closed position and grasped by the user when inserting the catheter into the blood vessel, and are thereafter moved to their open position. Movement of the wings to their open position actuates the releasable retainer mechanism, and the trocar is then drawn rearwardly so that its sharpened end is drawn into the catheter passage under the influence of the spring.

14 Claims, 2 Drawing Sheets

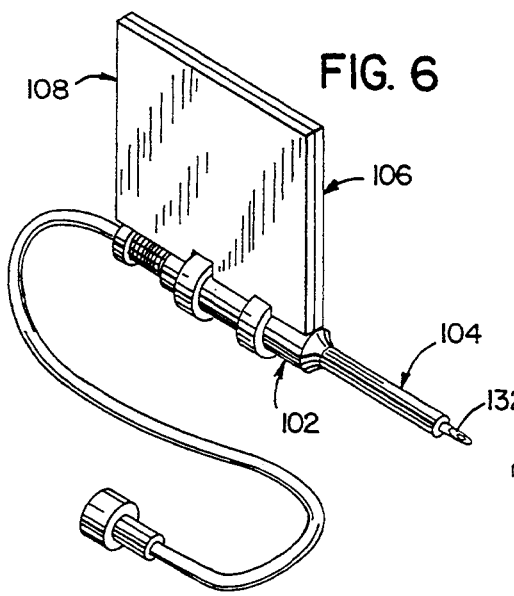
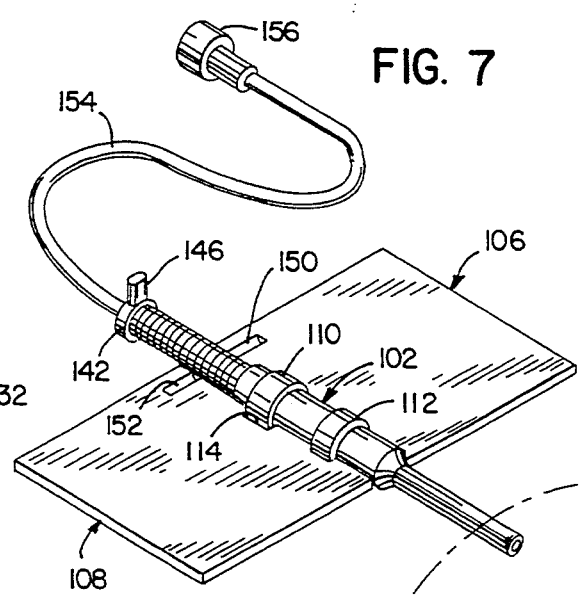
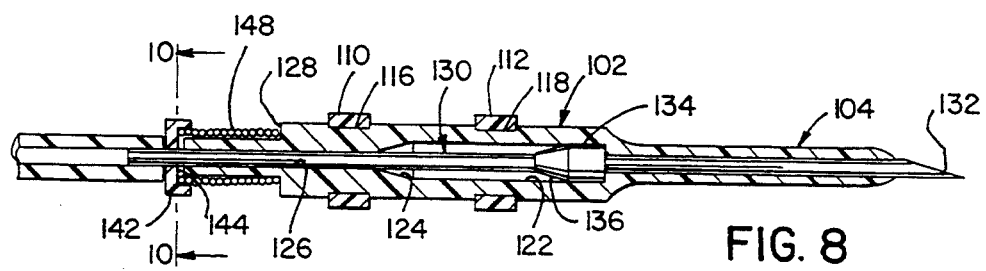
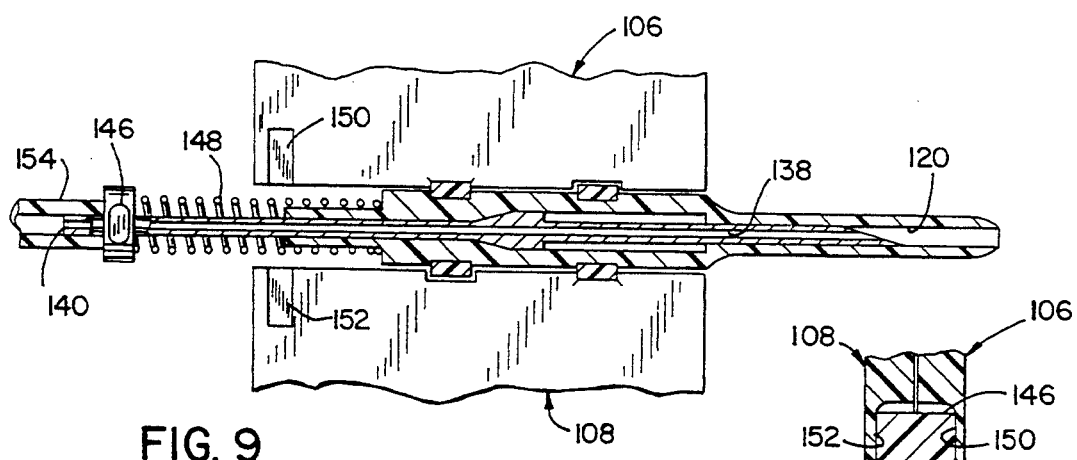
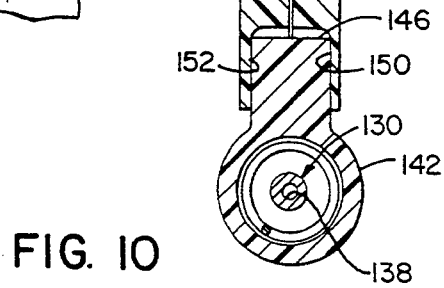

CATHETER SHARP RETRACTION SYSTEM

BACKGROUND AND SUMMARY

This invention relates to an intravenous catheter and trocar system, and more particularly to a system providing automatic retraction of the trocar after insertion of the catheter into a blood vessel.

Numerous patents disclose syringes which include a system for either automatically or semi-automatically retracting the syringe needle after use, to prevent accidental contact with the needle. One such syringe is shown in Lindemann, et al. U.S. Pat. No. 4,874,382, issued Oct.17, 1989. In addition Kuuli U.S. Pat. No. 4,747,831 shows a structure for manually retracting a catheter trocar after the trocar has been used to insert the catheter into a blood vessel of a patient.

It is an object of the present invention to provide an automatic arrangement for retracting a trocar after use of the trocar to insert a catheter into a blood vessel. It is a further object of the invention to incorporate an automatic trocar retraction system into various types of catheters. Yet another object of the invention is to provide a trocar retraction system which is relatively simple in concept and inexpensive to manufacture.

In accordance with the invention, an intravenous catheter system includes a catheter defining an internal passage and a trocar having an exposed sharpened end extending from the catheter passage when in an extended position, for use in placing the catheter into a patient's blood vessel. The system further includes an insertion device for manual engagement by a user for use in inserting the sharpened end of the trocar, and thereby the catheter, into the blood vessel. The insertion device includes structure defining an internal passage, and the trocar is releasably engaged with the insertion device when the trocar is in its extended position, to extend outwardly from the internal passage and through the catheter passage. Bias means is interconnected between the insertion device and the trocar, for urging retraction of the trocar from its extended position into the catheter passage. A releasable retainer mechanism functions to retain the trocar in its extended position prior to and during insertion of the catheter and the sharpened end of the trocar into the blood vessel, and for releasing engagement between the trocar and the insertion device in response to manual manipulation of the insertion device by the user after placement of the catheter into the blood vessel. Such manual manipulation of the insertion device functions to actuate the releasable retainer mechanism, to provide retraction of the trocar from its extended position into the catheter passage under the influence of the bias means.

In one form of the invention, the insertion device comprises a handle having one or more side walls defining the internal passage, with the handle being removably engaged with the catheter to provide disengagement of the handle from the catheter in response to manual manipulation of the handle after placement of the catheter into the blood vessel. Disengagement of the handle from the insertion device actuates the releasable retainer mechanism, to release engagement between the trocar and the handle and to provide retraction of the trocar from its extended position. The bias means comprises a spring or other biasing means interconnected between the trocar and the handle, to urge withdrawal of the trocar into and through the catheter passage and into the handle passage upon disengagement of the handle from the catheter. The handle passage opens onto an end of the handle, and a plug member is mounted within the handle passage toward the open end of the handle. The plug member defines a passage through which the trocar extends when in its extended position, and the spring is interposed between the trocar and the plug member to draw the trocar through the plug member passage upon disengagement of the handle from the catheter. A retraction head is mounted to the inner end of the trocar, and the spring is located between the plug member and the retraction head. The catheter includes an enlarged outer end portion defining an open outer end leading to an internal cavity, and an inner tubular end portion defining an open inner end and an internal passage extending between the internal cavity and the open inner end. The handle is removably engaged within the internal cavity defined by the enlarged outer end portion of the catheter. The handle plug member is removably engageable within the internal cavity defined by the enlarged outer end portion of the catheter, and the releasable retainer mechanism is mounted to the plug member and interposed between the trocar and the enlarged outer end portion of the catheter. The releasable retainer mechanism functions to release engagement between the handle and the trocar upon removal of the plug member from the internal cavity defined by the enlarged outer end portion of the catheter. The trocar retraction head includes a detent disposed within the plug member passage. The releasable retainer mechanism is engaged with the trocar detent to retain the trocar in its extended position, and is disengaged from the trocar detent upon removal of the plug member from the internal cavity to provide retraction of the trocar under the influence of the spring. In one form, the releasable retainer mechanism includes a pair of retainer wings mounted within a slot formed in the plug member, and engageable between the catheter and the trocar detent when the plug member is engaged within the internal cavity defined by the enlarged outer end portion of the catheter. Removal of the plug member from the catheter internal cavity releases engagement of the retainer wings between the catheter and the trocar detent.

In another form of the invention, the insertion device includes a pair of wings pivotably mounted for movement between a first position in which the wings are positioned substantially together and a second position in which the wings are moved apart. Manual movement of the wings between their first and second positions functions to actuate the releasable retainer mechanism, to release engagement between the trocar and the insertion device and to provide retraction of the trocar from its extended position. The insertion device includes a tubular body defining the internal passage within which the trocar is mounted, and the wings are pivotably mounted to the tubular body. The catheter is mounted to and extends outwardly from the tubular body, and defines an internal passage in communication with the internal passage defined by the body. The bias means, such as a spring, functions to withdraw the sharpened end of the trocar rearwardly into the catheter passage upon release of engagement between the trocar and the insertion device in response to movement of the wings away from their first position. The internal passage defined by the tubular body opens onto the rearward end of the body, and a rearward portion of the trocar extends outwardly from the rearward end of the body.

The releasable retainer mechanism includes a hub member mounted to the rearward portion of the trocar, and a detent arrangement interposed between the hub member and the wings for retaining the trocar in its extended position when the wings are in their first position, and for releasing engagement between the wings and the hub member when the wings are moved away from their first position toward their second position. The detent arrangement includes a stud mounted to the hub member, and a recess formed in each wing for receiving a portion of the stud when the wings are in their first position, and for releasing engagement between the stud and the wings when the wings are moved toward their second position. The tubular body defines an external shoulder, and the spring is interposed between the external shoulder and the hub member for urging retraction of the trocar into the catheter passage. The trocar includes a wedge-shaped stop portion disposed within the body passage, for cooperating with wedge structure disposed within the body passage for stopping rearward movement of the trocar under the influence of the bias means when engagement between the trocar and the insertion device is released. A tube may be connected to the rearward portion of the trocar, for communicating blood withdrawn from a patient to a blood collection receptacle.

The invention further contemplates a method of retracting the sharpened end of the trocar after placement of the catheter into the patient's blood vessel, substantially in accordance with the foregoing summary.

Various other features, objects and advantages of the invention will be made apparent from the following description taken together with the drawings.

BRIEF DESCRIPTION OF THE DRAWINGS

The drawings illustrate the best mode presently contemplated of carrying out the invention.

In the drawings:

FIG. 6 is a perspective view showing a butterfly-type catheter and trocar assembly incorporating an automatic trocar retraction system according to the invention, showing the wings moved together and the trocar in its extended position;

FIG. 7 is a view of the catheter and trocar assembly of FIG. 6 showing the wings moved apart and retraction of the trocar;

FIG. 8 is a partial longitudinal sectional view of the catheter and trocar assembly of FIGS. 6 and 7, showing the trocar in its extended position;

FIG. 9 is a partial longitudinal sectional view similar to FIG. 8, showing the trocar in its retracted position; and FIG. 10 is a section view taken along line 10—10 of FIG. 8.

DETAILED DESCRIPTION OF THE INVENTION

Figure 1:
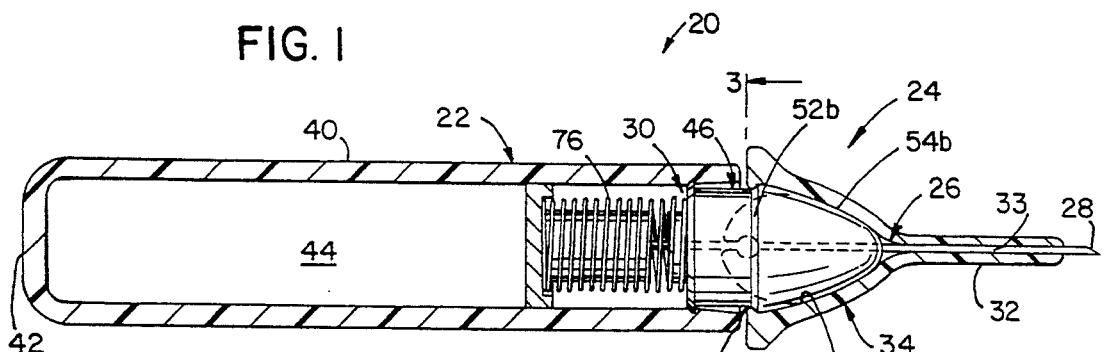
FIG. 1 is a longitudinal cross-sectional view of a catheter and trocar assembly incorporating a removable handle for providing automatic retraction of the trocar into the handle after disengagement of the handle from the catheter.

Referring to FIG. 1, a retractable catheter assembly 20 generally includes a handle 22, a catheter assembly 24, a trocar 26 terminating in a sharpened outer end 28, and a releasable retainer mechanism 30. catheter assembly 24 includes an inner tubular portion 32 defining a passage 33, which terminates in an open inner end from which trocar outer end 28 extends when trocar 26 is in its FIG. 1 position. Catheter assembly 24 further includes an enlarged outer end portion 34 which defines an open outer end and an internal cavity 36 which communicates between passage 33 defined by inner tubular portion 32 and the open outer end defined by catheter enlarged outer end portion 34. Catheter enlarged outer end portion 34 defines a peripheral inwardly extending lip 38 disposed between the open outer end of enlarged end portion 34 and internal cavity 36 defined thereby.

Handle 22 is cylindrical in shape, defining a side wall 40, and end wall 42, and an internal passage 44 which opens onto the inner end of handle 22.

A plug 46 is mounted to handle 22 at its open inner end. Plug 46 is in the form of a pair of identical plug halves, shown in FIGS. 2–5 at 46a, 46b. Plug halves 46a, 46b are identical in construction, Plug halves 46a, 46b each define a rear end including an outwardly extending lip 48a, 48b, respectively. Lips 48a, 48b are received within a circumferential internal groove formed in the internal surface of handle side wall 40 adjacent its open inner end, for mounting plug 46 to handle 22. The inner surface of handle side wall 40 adjacent the inner end of handle 22 is ramped, as shown at 50, for facilitating push-on insertion of plug halves 46a, 46b into the open inner end of handle 22 and engagement of lips 48a, 48b with the circumferential groove formed in the inner surface of handle side wall 40.

Figure 5:
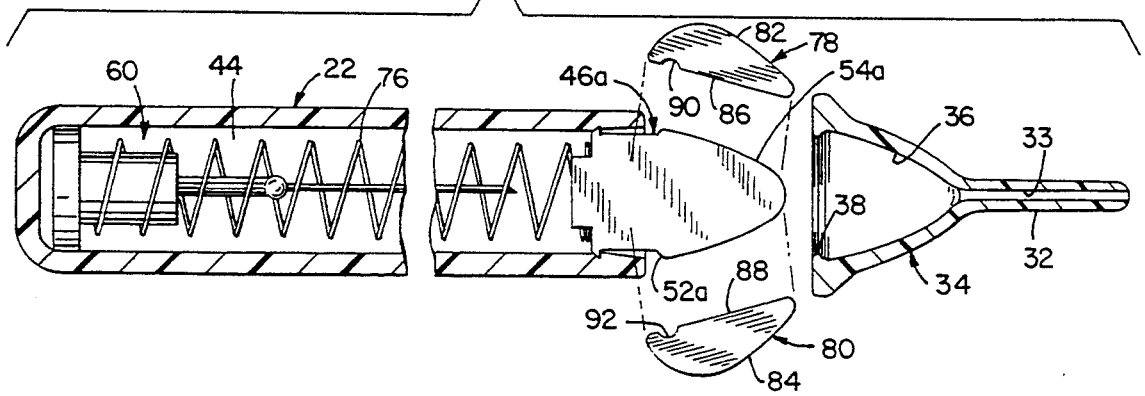
FIG. 5 is longitudinal sectional view of the trocar and catheter assembly of FIG. 1, showing retraction of the trocar into the handle after disengagement of the handle from the catheter.

Referring to FIGS. 1 and 5, plug halves 46a, 46b include peripheral shoulders 52a, 52bb, respectively, and nose portions 54a, 54b, respectively, extending outwardly from shoulders 52a, 52b. Nose portions 54a, 54b are shaped similarly to internal cavity 36 defined by catheter enlarged outer end portion 34.

Figure 2:
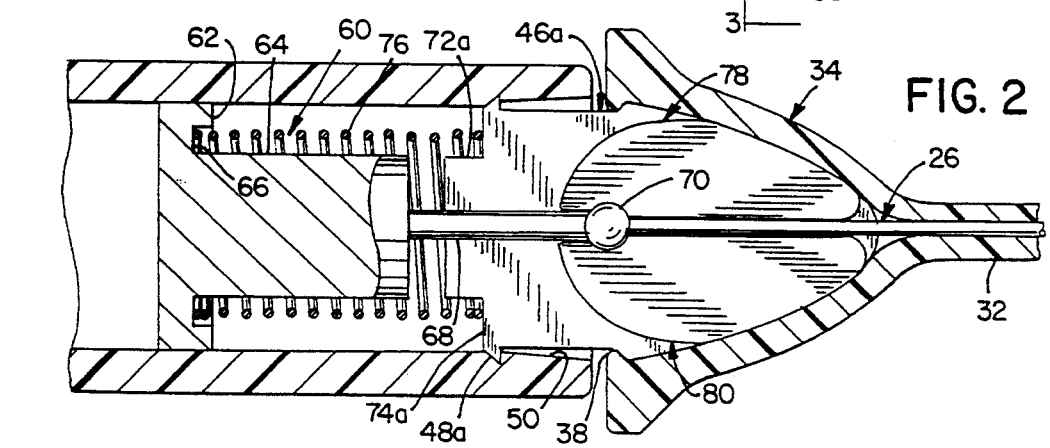
FIG. 2 is an enlarged portional sectional view of the catheter and trocar assembly of FIG. 1, showing the releasable retainer mechanism maintaining the trocar in its extended position.
Figure 3:
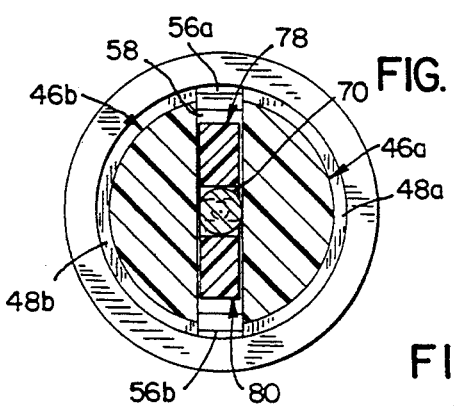
FIG. 3 is a section view taken along line 3—3 of FIG. 1.
Figure 4:
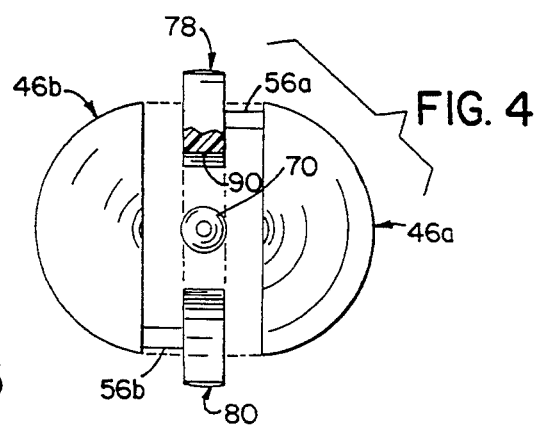
FIG. 4 is an exploded end elevation view of the releasable retainer mechanism plug member and wings of the catheter and trocar system of FIG. 1.

As shown in FIGS. 3 and 4, plug halves 46a, 46b further define spacers 56a, 56b, respectively. Spacers 56a, 56b function to space plug halves 46a, 46b apart from each other when plug halves 46a, 46b are mounted to handle 22, to define a slot 58 therebetween. With plug halves 46a, 46b mounted within the open inner end of handle 22 as described, shoulders 52a, 52b are spaced just outwardly from the inner end of handle 22 with nose portions 54a, 54b extending therefrom. Catheter 24 is engaged with plug halves 46a, 46b as shown in FIGS. 1 and 2, with catheter lip 38 being placed over shoulders 52a, 52b for retaining catheter 24 in place. Nose portions 54a, 54b of plug halves 46a, 46b, respectively are received within internal cavity 36 defined by catheter enlarged outer end portion 34.

Referring to FIG. 2, trocar 26 is mounted to a retraction head, shown generally at 60. Retraction head 60 is located within handle passage 44, and includes a flange 62 in close proximity to the inner surface defined by handle side wall 40. Flange 62 extends outwardly from a main body portion 64. A circumferential groove 66 is formed in flange 62 adjacent body portion 64.

Body portion 64 further defines a forward extension 68 through which trocar 26 extends. A circumferential spherical detent 70 is formed at the forward end of extension 68.

As shown in FIGS. 1 and 2, plug halves 46a, 46b includes bosses 72a, 72b extending rearwardly from rear surfaces 74a, 74b, respectively. A spring 76 is interposed between retraction head 60 and plug 46. The forward end of spring 76 is engaged with rear surfaces 74a, 74b of plug halves 46a, 46b, respectively, with bosses 72a, 72b received within spring 76. The rearward end of spring 76 is received within groove 66 formed in flange 62 of retraction head 60.

A pair of retainer wings, shown at 78, 80 (FIGS. 2-5) are received within slot 58 between plug halves 46a, 46b. Wings 78, 80 define outer surfaces 82, 84, respectively, and facing inner surfaces 86, 88, respectively. Retaining recesses 90, 92 are formed in facing surfaces 86, 88, respectively. When wings 78, 80 are in their position as shown in FIGS. 1-3, detent 70 is received within retaining recess 90, 92. Wings 78, 80 are trapped between trocar 26 and the inner wall of catheter enlarged outer end portion 34, to thereby maintain trocar 26 in its extended position against the rearward bias exerted by spring 76.

In operation, catheter and trocar assembly 20 functions as follows. Initially, trocar 26 is in its armed condition, as shown in FIGS. 1 and 2 wherein trocar sharpened end 28 protrudes outwardly from the end of catheter inner tubular portion 32. With catheter and trocar assembly 20 in this condition, the user grasps handle 22 and enlarged outer end portion 34 of catheter 24 to place inner tubular portion 32 of catheter 24 into a patient's blood vessel. Sharpened outer end 28 of trocar 26 pierces the patient's skin for allowing inner tubular portion 32 of catheter 24 to penetrate the skin during placement of catheter 24, trocar 26 is maintained in its extended position as shown in FIGS. 1 and 2 against the force of spring 76, by retainer wings 78, 80 remaining in their FIG. 2 position, as previously described. After inner tubular portion 32 of catheter 24 is in place in the patient's blood vessel, the user grasps handle 22 and catheter enlarged outer end portion 34 to remove handle 22 from catheter 24 with a pull-apart motion. Plug shoulders 52a, 52b are disengaged from catheter lip 38, to allow plug member nose portions 54a, 54b to be withdrawn from internal cavity 36 defined by catheter enlarged outer end portion 34. Upon such disengagement of plug 46 from catheter 24, retainer wings 78, 80 are no longer trapped between trocar 26 and the inner wall of catheter enlarged outer end portion 34, and thereby release retention of detent 70. Spring 76 then extends to its position as shown in FIG. 5, to withdraw retraction head 60 into handle passage 44, and thereby withdrawal of trocar 26 through catheter passage 33 and through internal cavity 36 defined by catheter enlarged outer end portion 34. Trocar 26 also passes rearwardly through slot 58 between plug member halves 46a, 46b, and is thereafter completely enclosed within handle passage 44 to prevent accidental contact with trocar sharpened end 28. Handle 22 with trocar 26 contained therein is then discarded, and a typical fitting is engaged with catheter enlarged outer end portion 34 for withdrawing blood from the patient or for providing intravenous introduction of a fluid into the patient's blood vessel.

FIG. 2 illustrates another embodiment of the invention, in the form of a butterfly trocar and catheter assembly 100. Assembly 100 includes a tubular body 102 which defines a forwardly extending catheter portion 104. A pair of wings 106, 108 are pivotably mounted to body 102. Referring to FIGS. 6-8, a ring 110 is mounted to wing 106, and a ring 112 is mounted to wing 108. Ring 110 passes through a slot 114 formed in wing 108, and in a like manner ring 112 passes through a slot (not shown) formed in wing 106. Rings 110, 112 are mounted within grooves 116, 118 formed in the outer surface of body 102, for pivotably mounting wings 106, 108 to body 102.

Referring to FIGS. 8 and 9, catheter portion 104 defines an internal passage 120 which opens onto the forward end of catheter portion 104. Passage 120 opens rearwardly into an internal passage 122 formed in body 102, which includes wedge structure 124 at its rearward end. A rear passage 126 is formed in body 102, extending rearwardly from wedge structure 124 and opening onto the rearward end of body 102. A circumferential external shoulder 128 is formed on body 102.

A trocar, shown generally at 130, is mounted to body 102. Trocar 130 defines a sharpened outer end 132, which extends outwardly from the end of catheter portion 104 when trocar and catheter assembly 100 is in its armed condition as shown in FIGS. 6 and 8. Trocar 130 includes a boss 134 provided with a wedge surface 136. Trocar 130 further includes a longitudinal internal passage 138 (FIG. 9) which extends between and opens onto sharpened outer end 132 and the rear end of trocar 130, shown at 140.

A hub 142 is mounted to trocar 130 adjacent its rear end 140. Hub 142 is provided with a circumferential groove 144 surrounding trocar 130. Hub 142 further includes an upstanding stud 146 (FIGS. 7, 9, and 10). A spring 148 is received within groove 144 of hub 142, and is seated at is opposite end against shoulder 128 defined by body 102. Spring 148 functions to urge trocar 130 inwardly away from its extended position.

Referring to 7, 9 and 10, a pair of slots, 150, 152 are formed in wings 106, 108, respectively. Slots 150, 152 receive stud 146 therewithin when wings 106, 108 are in their closed position, as shown in FIG. 6.

In operation, the embodiment of FIGS. 6-10 functions as follows. Prior to placement of catheter portion 104 and trocar sharpened end 132 into a patient's blood vessel, wings 106, 108 are in their closed position of FIG. 6. In this position, trocar 130 is maintained in its FIG. 8 position, with sharpened end 132 extending outwardly from the forward end of catheter portion 104, by stud 146 being received within slots 150, 152 formed in wings 106, 108, respectively as shown in FIG. 10. This maintains trocar 130 in its FIG. 8 position against the rearward biasing force applied by spring 148 to trocar 130. The user then grasps wings 106, 108 in their closed position of FIG. 2, and places catheter portion 104 into a patient's blood vessel, with trocar sharpened end 132 piercing the patient's skin to facilitate entry of catheter portion 104 into the blood vessel. Wings 106, 108 are then moved to their open position of FIG. 7 against the surface of the patient's skin. Typically, a piece of tape is then applied over wings 106, 108 to maintain catheter portion 104 in place within the blood vessel.

Upon unfolding wings 106, 108 from their FIG. 6 position and moving wings 106, 108 toward their FIG. 7 position, stud 146 is disengaged from slots 150, 152 in wings 106, 108, respectively. This releases engagement between the insertion device and trocar 130, and trocar 130 is then forced to its FIG. 9 position under the influence of spring 148 until engagement of trocar wedge surface 136 with wedge structure 124 at the rearward end of passage 122. Such movement of trocar 130 results in trocar sharpened end 132 being drawn into passage 120 defined by catheter portion 104. Fluid communication is established with the patient's blood vessel through trocar passage 138 and passage 120 defined by catheter portion 104. Withdrawal of trocar sharpened end 132 into catheter portion passage 120 prevents accidental contact with trocar sharpened end 132 after withdrawal of catheter portion 104 from the patient.

A tube 154 is connected to the rearward end of trocar 130, and a receptacle 156 is mounted to the opposite end of tube 154. In this manner, blood can be withdrawn from the patient by connecting a blood collection device to receptacle 156. Alternatively, fluid can be introduced into the patient's blood vessel by connecting an IV set to receptacle 156.

Various alternatives and embodiments are contemplated as being within the scope of the following claims particularly pointing out and distinctly claiming the subject matter regarded as the invention.

We claim:

1. In an intravenous catheter system including a catheter defining an internal passage and a catheter insertion member having an exposed sharpened end extending from the catheter passage when in an extended position, for use in placing the catheter into a blood vessel of a patient, the improvement comprising:

an insertion device for manual engagement by a user for use in inserting the sharpened end of the catheter insertion member into the patient's blood vessel to establish communication therewith by the catheter, wherein the catheter is fixedly secured and extends from the insertion device, and wherein the catheter insertion member is releasably engaged with the insertion device when in its extended position so as to extend outwardly from the internal passage and through the catheter passage;

bias means interconnected between the insertion device and the catheter insertion member for urging retraction of the catheter insertion member from its extended position into the catheter passage; and a releasable retainer mechanism for retaining the catheter insertion member in its extended position prior to and during insertion of the catheter and the insertion member sharpened end into the blood vessel, and for releasing engagement between the catheter insertion member and the insertion device in response to manual manipulation of the insertion device by the user after placement of the catheter into the blood vessel, to provide retraction of the catheter insertion member from its extended position into the catheter passage under the influence of the bias means, wherein the catheter functions to enclose the insertion member sharpened end its retraction into the catheter passage.

2. The improvement of claim 1, wherein the insertion device comprises a pair of wings pivotably mounted for movement between a first position in which the wings are positioned substantially together and a second position in which the wings are moved apart, wherein manual movement of the wings between the first and second positions functions to actuate the releasable retainer mechanism to release engagement between the catheter insertion member and the insertion device to provide retraction of the catheter insertion member from its extended position.

3. The improvement of claim 2, wherein the insertion device further comprises a tubular body to which the wings are pivotably mounted, wherein the tubular body defines an internal passage within which the catheter insertion member is mounted, and wherein the catheter is mounted to and extends outwardly from the tubular body, the catheter defining an internal passage in communication with the internal passage defined by the body, and wherein the bias means functions to withdraw the sharpened end of the catheter insertion member rearwardly into the catheter passage upon release of engagement between the catheter insertion member and the insertion device.

4. The improvement of claim 3, wherein the tubular body defines a first end and a second end, wherein the catheter extends from the first end of the body and wherein the internal passage defined by the body opens onto the second end of the body, and wherein a rearward portion of the catheter insertion member extends from the body internal passage outwardly from the second end of the body.

5. In an intravenous catheter system including a catheter defining an internal passage and a catheter insertion member having an exposed sharpened and extending from the catheter passage when in an extended position, for use in placing the catheter into a blood vessel of a patient, the improvement comprising:

an insertion device for manual engagement by a user for use in inserting the sharpened end of the catheter insertion member into the patient's blood vessel to establish communication therewith by the catheter, the insertion device including a tubular body defining first and second ends and an internal passage within which the catheter insertion member is mounted, wherein the catheter insertion member is releasably engaged with the insertion device when in its extended position so as to extend outwardly from the internal passage and through the catheter passage, wherein the insertion device further comprises a pair of wings pivotably mounted to the tubular body for movement between a first position in which the wings are positioned substantially together and a second position in which the wings are moved apart, and wherein the catheter is mounted to and extends outwardly from the first end of the tubular body, the catheter defining an internal passage in communication with the internal passage defined by the body, and wherein the internal passage defined by the body opens onto the second end of the body and a rearward portion of the catheter insertion member extends from the body internal passage outwardly from the second end of the body;

bias means interconnected between the insertion device and the catheter insertion member for urging retraction of the insertion member from its extended position into the catheter passage; and a releasable retainer mechanism for retaining the catheter insertion member in its extended position prior to and during insertion of the catheter and the inserting member sharpened end into the blood vessel, and for releasing engagement between the insertion member and the insertion device in response to manual manipulation of the insertion device by the user after placement of the catheter into the blood vessel, to provide retraction of the insertion member from its extended position into the catheter passage under the influence of the bias means, wherein the releasable retainer mechanism comprises a hub member mounted to the rearward portion of the catheter insertion member and a detent arrangement interposed between the hub member and the wings for retaining the insertion member in its extended position when the wings are in their first position, and for releasing engagement between the wings and the hub member when the wings are moved away from their first position toward their second position;

wherein the manual movement of the wings between the first and second positions functions to actuate the releasable retainer mechanism to release engagement between the insertion member and the insertion device, wherein the bias means functions to withdraw the sharpened end of the insertion member rearwardly into the catheter passage upon release of engagement between the insertion member and the insertion device to provide retraction of the insertion member from its extended position.

6. The improvement of claim 5, wherein the detent arrangement comprises a stud mounted to the hub member, and a recess formed in each wing for receiving a portion of the stud when the wings are in their first position, and for releasing engagement between the stud and the wings when the wings are moved away from their first position toward their second position.

7. The improvement of claim 5, wherein the tubular body defines an external shoulder, and wherein the bias means comprises a spring interposed between the external shoulder and the hub.

8. In an intravenous catheter system including a catheter defining an internal passage and a catheter insertion member having an exposed sharpened end extending from the catheter passage when in an extended position, for use in placing the catheter into a blood vessel of a patient, the improvement comprising:

an insertion device for manual engagement by a user for use in inserting the sharpened end of the catheter inserting member into the patient's blood vessel to establish communication therewith by the catheter, the insertion device including a tubular body defining first and second ends and an internal passage within which the catheter insertion member is mounted, wherein the catheter insertion member is releasably engaged with the insertion device when in its extended position so as to extend outwardly from the internal passage and through the catheter passage, wherein the inserting device further comprises a pair of wings pivotably mounted to the tubular body for movement between a first position in which the wings are positioned substantially together and a second position in which the wings are moved apart, and wherein the catheter is mounted to and extends outwardly from the first end of the tubular body, the catheter defining an internal passage in communication with the internal passage defined by the body, and wherein the internal passage defined by the body opens onto the second end of the body, and wherein a rearward portion of the catheter insertion member extends from the body internal passage outwardly from the second end of the body;

bias means interconnected between the insertion device and the catheter inserting member for urging retraction of the insertion member from its extended position into the catheter passage; and a releasable retainer mechanism for retaining the catheter inserting member in its extended position prior to and during insertion of the catheter and the insertion member sharpened end into the blood vessel, and for releasing engagement between the inserting member and the insertion device in response to manual manipulating of the insertion device by the user after placement of the catheter into the blood vessel, to provide retraction of the insertion member from its extended position into the catheter passage under the influence of the bias means;

wherein the manual movement of the wings between the first and second positions functions to actuate the releasable retainer mechanism to release engagement between the insertion member and the insertion device, wherein the bias means functions to withdraw the sharpened end of the insertion member rearwardly into the catheter passage upon release of engagement between the insertion member and the inserting device to provide retraction of the inserting member from its extended position;

wherein the insertion member including a stop portion disposed within the body passage for cooperating with the structure of the body adjacent the body passage to stop rearward movement of the insertion member under the influence of the bias means when engagement between the insertion member and the insertion device is released.

9. The improvement of claim 8, wherein the insertion member stop portion comprises wedge structure disposed within the body passage, wherein the body passage includes a rear wedge surface engaged by the wedge structure of the insertion member upon rearward movement of the insertion member, to stop rearward movement of the insertion member.

10. The improvement of claim 4, further comprising a blood collection receptacle and a tube extending between the blood collection receptacle and the rearward portion of the catheter insertion member for communicating blood from the catheter insertion member to the blood collection receptacle.

11. In an intravenous catheter system including a catheter defining an internal passage and a needle having a lumen and an exposed sharpened end extending from the catheter passage when in an extended position, for use in placing the catheter into a blood vessel of a patient, the improvement comprising:

an insertion device for manual engagement by a user for use in inserting the sharpened end of the needle into the patient's blood vessel to establish communication therewith by the catheter, wherein the needle is releasably engaged with the insertion device when in its extended position so as to extend outwardly from the catheter passage;

bias means interconnected between the insertion device and the needle for urging retraction of the needle from its extended position into the catheter passage; and a releasable retainer mechanism for retaining the needle in its extended position prior to and during insertion of the catheter and the needle sharpened end into the blood vessel, and for releasing engagement between the needle and the insertion device in response to manual manipulation of the insertion device by the user after placement of the catheter into the blood vessel, to provide retraction of the needle to a retracted position from its extended position into the catheter passage under the influence of the bias means, wherein the needle in its retracted position provides communication with the catheter passage through the needle lumen.

12. The improvement of claim 11, wherein the needle includes a rearward end opposite the sharpened end, and wherein the needle lumen extends between and opens onto the sharpened end and the rearward end to establish fluid communication therebetween.

13. The improvement of claim 12, wherein the insertion device includes an internal passage within which the needle is mounted, wherein the needle rearward end extends from the insertion device internal passage and is interconnected with a conduit for communicating a fluid between the conduit and the blood vessel of a patient via the needle lumen and catheter passage.

14. The improvement of claim 11, further comprising a hub mounted to the needle externally of the insertion device, and wherein the bias means comprises a spring interposed between the hub and the insertion device.

* * * * *

UNITED STATES PATENT AND TRADEMARK OFFICE
CERTIFICATE OF CORRECTION

PATENT NO. : 5,376,075
DATED : December 27, 1994
INVENTOR(S) : VICTOR M. HAUGHTON ET AL It is certified that error appears in the above-identified patent and that said Letters Patent is hereby corrected as shown below:

Claim 1, col. 7, line 40, after "secured" insert -- to --; Claim 8, col. 9, line 56, delete "inserting" and substitute therefor -- insertion --; Claim 8, col. 10, line 4, delete "inserting" and substitute therefor -- insertion --; Claim 8, col. 10, line 8, delete "inserting" and substitute therefor -- insertion --; Claim 8, col. 10, line 12, delete "inserting" and substitute therefor -- insertion --; Claim 8, col. 10, line 27; delete "inserting" and substitute therefor -- insertion --; Claim 8, col. 10, line 28, delete "inserting" and substitute therefor -- insertion --; Claim 8, col. 10, line 29, delete "including" and substitute therefor -- includes --.

Signed and Sealed this

Twenty-first Day of March, 1995

*Attest:*

BRUCE LEHMAN

*Attesting Officer*  Commissioner of Patents and Trademarks